United States Patent
Valikai et al.

[11] Patent Number: 5,948,005
[45] Date of Patent: Sep. 7, 1999

[54] MULTI-EVENT BIN HEART RATE HISTOGRAM FOR USE WITH AND IMPLANTABLE PACEMAKER

[75] Inventors: Kenneth Valikai, Palos Verdes Pen; Gregory Bevan, Pacoima, both of Calif.

[73] Assignee: Pacesetter, Inc., Sylmar, Calif.

[21] Appl. No.: 08/789,865

[22] Filed: Jan. 28, 1997

[51] Int. Cl.⁶ .......................... A61N 1/37; A61B 5/0452
[52] U.S. Cl. ................... 607/32; 607/9; 607/30
[58] Field of Search .................. 607/9, 27, 28, 607/30, 32

[56] References Cited

U.S. PATENT DOCUMENTS

| | | | |
|---|---|---|---|
| 4,513,743 | 4/1985 | van Arragon et al. | 128/419 PG |
| 4,791,936 | 12/1988 | Snell et al. | 128/697 |
| 4,809,697 | 3/1989 | Causey, III et al. | 128/419 PT |
| 4,825,869 | 5/1989 | Samsor et al. | 607/27 |
| 4,940,052 | 7/1990 | Mann et al. | 128/419 PG |
| 5,088,488 | 2/1992 | Markowitz et al. | 607/27 |
| 5,309,919 | 5/1994 | Snell et al. | 607/26 |
| 5,330,513 | 7/1994 | Nichols et al. | 607/32 |
| 5,431,691 | 7/1995 | Snell et al. | 607/27 |
| 5,456,692 | 10/1995 | Smith, Jr. et al. | 607/31 |
| 5,487,755 | 1/1996 | Snell et al. | 607/27 |

*Primary Examiner*—William E. Kamm
*Assistant Examiner*—Carl H. Layno

[57] ABSTRACT

Event/rate data gathered by an implantable pacemaker is displayed in a histogram format as a function of heart rate and event type, with multiple events being included in the display of each rate bin of the histogram. Event types include a paced event, a sensed event, or a premature ventricular event (PVE). Two types of histograms are provided: (1) a heart rate histogram that shows the occurrence of each event type in each heart rate bin as a function of the percent of total events in all heart rate bins; and (2) a histogram that shows event type distribution by rate bin.

40 Claims, 8 Drawing Sheets

MULTI-EVENT BIN HEART RATE HISTOGRAM FOR USE WITH AND IMPLANTABLE PACEMAKER

FIELD OF THE INVENTION

The present invention relates to implantable medical devices and methods, and more particularly to an implantable pacemaker or pacemaker system wherein event/rate data associated with the operation of the pacemaker is gathered and displayed as a function of heart rate in a histogram having multi-event bins. Such multi-event bin heart rate histogram facilitates discernment of certain types of events that might otherwise go unnoticed in the event/rate data or conventional heart rate histogram.

BACKGROUND OF THE INVENTION

One of the most common types of implantable medical devices in use today is the implantable pacemaker. Modern pacemakers are small, battery-powered electronic devices that monitor the activity of the heart to determine when the heart is naturally beating, and provide stimulation pulses to the heart when the heart is not naturally beating, thereby maintaining a prescribed heart rhythm or rate. Advantageously, a pacemaker may be implanted in a patient, and coupled to the patient's heart via appropriate pacemaker leads that are also implanted. By implanting the pacemaker and leads, the pacemaker becomes an integral part of the patient, and the patient is able to maintain a substantially normal life style without the bother and worry that typically accompany the use of external (non-implanted), life-sustaining medical devices.

Nearly all implantable pacemakers in use today, as well as similar implantable medical devices, can be configured by the attending physician in the physician's office. The process of configuring a pacemaker is commonly referred to as "programming". The programming process uses non-invasive telemetry to customize the operation of the pacemaker to fit the individual needs of the patient. Customization is achieved by adjusting a set of "pacemaker parameters" to values that cause the pacemaker to work in an optimum way for the particular patient within whom the device has been implanted.

Disadvantageously, as the complexity of new implantable devices has evolved over the past several years, it has become increasingly difficult for the attending physician, or other medical personnel, to determine how the pacemaker should be programmed in order to provide the most effective therapy for a given patient. This difficulty is particularly manifest with recent-generation pacemakers that tend to be more automatic and autonomous than earlier-generation pacemakers, and that respond to input control signals from one or more sensors that attempt to assess the physiological needs of the patient.

A significant factor that makes the optimum programming of recent-generation pacemakers more difficult is the variation in each of the sensor inputs from patient to patient. Such variation is caused by numerous factors, including the patient's physical structure, age, sex, the implant site, the particular disease or malady the patient has and its progression within the patient's heart or other body tissue, the patient's physical condition and associated activity level, the drugs being taken by the patient to treat his or her condition, etc. Thus, to appropriately program the pacemaker for a given patient, the physician must anticipate how the pacemaker will operate given all of these variables, and given all the environments and activities that the patient is expected to encounter. Programming a modern pacemaker may thus comprise an extremely formidable task, for which task there is a critical need for programming aids to assist the physician in anticipating the pacemaker response for each particular patient.

An important aid known in the art to help properly program an implantable pacemaker, and to facilitate the physician's understanding of the pacemaker's programmed operation as its interacts with the patient's natural cardiac activity, is the sensing and recording of various pacemaker and cardiac events, including the rate of occurrence of such events (hereafter "event/rate data"). Once such event/rate data has been collected, it may be presented in a histogram format, as taught, e.g., in U.S. Pat. No. 4,513,743 (van Arragon et al.). The van Arragon '743 patent teaches various types of single-event histograms which display or show the distribution of a single event as a function of a specified class. The specified class may be, e.g., an atrial rate, with each class comprising a particular range of atrial rates, e.g., 0–50 ppm, 51–60 ppm, 61–70 ppm, etc. The van Arragon '743 patent further teaches that two such single event histograms may be shown in parallel, as shown in FIG. 3(d) of the '743 patent, or that a plurality of such single event histograms may be shown in series (time sequence), as shown in FIG. 3(e) of the '743 patent.

It is further known to display the event/rate data in an event count table, as taught, e.g., in U.S. Pat. No. 5,309,919 (Snell et al.), incorporated herein by reference. The Snell '919 patent teaches gathering of such event/rate data over a significant period of time, e.g., several hours, days, or months, and then (when requested by a physician or other medical personnel) downloading the event/rate data to the pacemaker's programming device ("programmer") for further processing and display. In particular, the Snell '919 patent teaches that such event/rate data, after having been gathered and downloaded, may be displayed in the form of an event/rate table. An event/rate table of the type created and displayed in the Snell '919 patent is shown, for example, in FIG. 6.

Unfortunately, the information conveyed in a conventional heart rate histogram, such as is taught in the van Arragon '743 patent, is somewhat incomplete because only a single event is displayed in each histogram, while other events are either not displayed, or must be displayed in a different histogram which is displayed separately, or in parallel, or in series with, other histograms. Such multiple single-event histogram displays, while potentially conveying a great deal of information, do not collectively convey such information in a format that is very easy for an attending physician (or other medical personnel) to readily comprehend, or that is easy to correlate with the other information. Further, while the data presented in an event/rate table, such as is developed in the Snell '919 patent, and is shown in FIG. 6 herein, is very complete, such data is not particularly easy to comprehend, visualize or correlate without careful analysis thereof.

In view of the above, it is evident that what is needed are improved techniques and methods of presenting existing event/rate data in a way that makes such event/rate data much easier to quickly comprehend and correlate, thereby facilitating its use in evaluating the performance of the patient's pacemaker. Once the data/rate information is properly understood, it thereafter serves a more useful purpose in correctly guiding subsequent reprogramming of the pacemaker, as required, and in aiding the development of appropriate treatment therapy for the patient.

SUMMARY OF THE INVENTION

The present invention advantageously addresses the above and other needs by providing a heart rate histogram having multi-event bins that graphically conveys event/rate data gathered by an implantable pacemaker as a function of heart rate and event type. The multiple events included in each bin of the heart rate histogram include: a paced event, a sensed event, or a premature ventricular event (PVE). Heart rate bins define the various heart rate zones within which each of the listed events are classified, and the number of occurrences of each event type in each heart rate bin is graphically displayed as part of the histogram. Two types of multi-event bin histograms are provided: (1) a heart rate histogram that shows the different event types occurring in each heart rate bin as a percentage of the total events occurring in all of the heart rate bins; and (2) a histogram that shows the distribution of each event type within each rate bin. The event distribution may also be displayed as a percentage of the total time period that data was collected. Advantageously, each histogram type is a single histogram, yet each displays within each rate bin all of the event types, clearly marked, so that the multi-event/rate data is quickly conveyed and easily understood at a glance. The combination of the two histograms is particularly helpful in conveying, in an easy to understand and quick to comprehend format, all of the relevant data contained within the event/rate table.

Thus, in accordance with one aspect of the invention, an implantable pacemaker senses and records event/rate data. At the appropriate time, such event/rate data is downloaded to an external programming device, where it is processed and displayed and/or printed by the programming device in a format that facilitates a physician's ability to quickly and comprehensively assess the performance of the implanted pacemaker over the relevant data-gathering time period, which data-gathering time period may be on the order of days, weeks, or months.

More particularly, the present invention provides an external programmer, or equivalent data receiving and data processing device, that is configured to receive, process, and display (e.g., print) event/rate data gathered by the pacemaker as a heart rate histogram having multi-event bins. Such multi-event bin heart rate histogram is divided into a multiplicity of heart rate bins, or rate zones, each of which provides an indication of the number and/or distribution of multiple types of events occurring within each rate bin during the relevant data-gathering time period.

In a first embodiment of the multi-event bin heart rate histogram of the present invention, multiple types of events are displayed in each heart rate bin as a function of the percent of total events that occurred during the total data-gathering time period. The events occurring within each rate bin are represented as a bar graph, with the different types of events being represented as separate identifiable segments or portions of the bar. The total length of the bar (including all segments) of a given rate bin is representative of the percent (or ratio) of the total events for that rate bin to the total events for all rate bins.

In a second embodiment of the multi-event bin heart rate histogram of the present invention, each rate bin is divided into a display of 100% of the events in each bin, thereby allowing certain specific types of events that occur as part of the bin event data to be readily discerned, even though such specific types of events may have a relatively low rate of occurrence, and may thus be indiscernible (buried within the heart rate histogram data) in the first histogram embodiment described above.

Thus, it is a feature of the invention to present or display event/rate data gathered by a pacemaker in an easy-to-understand graphical representation, and in particular, to present such data in a heart rate histogram that distinguishes the occurrence of multiple events within each heart rate bin of the histogram.

It is a further feature of the invention, in accordance with one embodiment thereof, to display a heart rate histogram that shows the occurrence of the multiple event data in each rate bin of the histogram as a percent of the total events that have occurred in all of the rate bins over the total time that the event/rate data was gathered.

It is an additional feature of the invention, in accordance with another embodiment thereof, to display the relative distribution of all of the event types in each rate bin.

It is an additional feature of the invention to provide heart rate/event data of a pacemaker patient in a histogram format that enables an attending physician (or other medical personnel), with just a glance or two at the histogram, to quickly and correctly comprehend the performance of the pacemaker and its interaction with the patient, thereby guiding the physician (or other medical personnel) to the most effective pacemaker therapy for the patient as the pacemaker is programmed and reprogrammed.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention relates to a particular technique, method, or format, for presenting heart rate event data that is sensed and gathered by an implantable pacemaker over a substantial period of time, e.g., days or weeks or months. Once a sufficient amount of the heart rate event data has been gathered, it may then be downloaded to an external programmer where it is displayed in the heart rate histograms having multi-event rate bins that comprise the present invention. It is important to note that the present invention is not directed to the implantable pacemaker that senses and gathers the heart rate data, nor is it directed, per se, to the programmer used with such pacemaker. In fact, any conventional pacemaker that has the capability of gathering heart rate event data, and any conventional programmer that has the ability to receive and display such data, such as the pacemaker and programmer disclosed, e.g., in U.S. Pat. No. 5,309,919 (previously incorporated herein by reference), can be configured to practice the present invention.

To better understand how a pacemaker and programmer may be configured to practice the present invention, it will first be helpful to review the main components, and basic operation, of a pacing system, i.e., the pacemaker and the programmer. Accordingly, the following overview of a pacemaker and programmer is presented.

The Pacemaker

Figure 1:
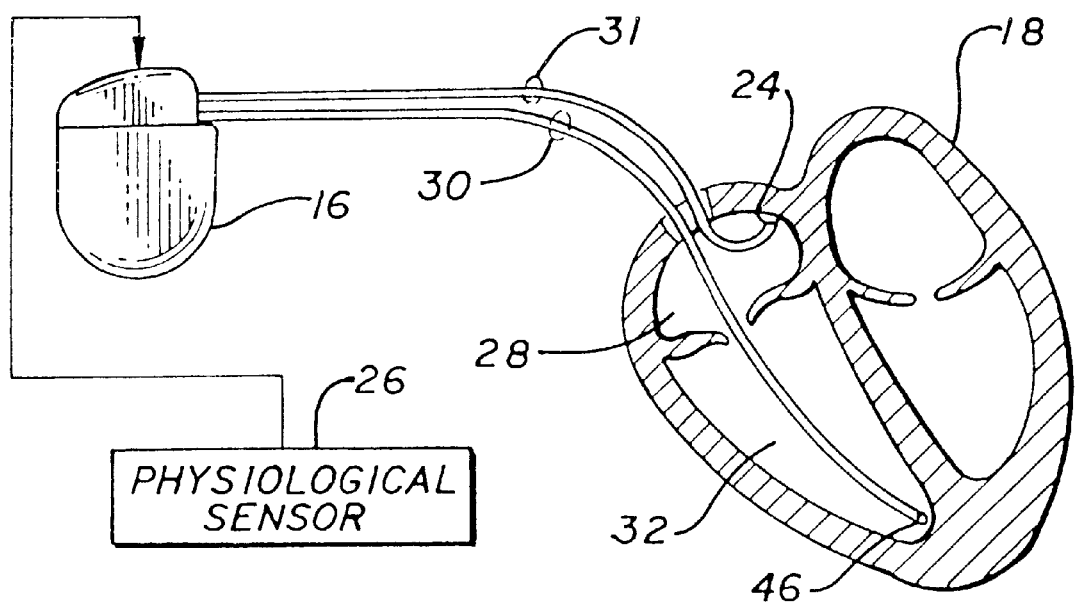
FIG. 1 shows an implantable pacemaker coupled to the heart.

The pacemaker side of a pacing system is shown in FIG. 1. As seen in FIG. 1, an implantable pacemaker 16 may have a physiological sensor 26 associated therewith. (Note, not all pacemakers need have a physiological sensor 26; but many do. Thus, although a sensor 26 is shown coupled to the pacemaker 16 in FIG. 1, it is to be understood that the present invention may be used with pacemakers that do not have a sensor 26 coupled thereto; or to pacemakers wherein such a sensor is inside of the pacemaker 16; or to pacemakers wherein such sensor 26, if present, has been programmed to an OFF or PASSIVE mode.)

The pacemaker 16 is coupled to a heart 18 by way of pacing leads 30 and 31. The pacing lead 30 has an electrode 46 positioned in the right ventricle 32 of the heart 18. The lead 30 is thus typically referred to as the ventricular lead, and the signals generated by the pacemaker for delivery to the heart through electrode 46 over lead 30, or the signals sensed through electrode 46 and the lead 30, are processed by circuits in what is known as the ventricular channel of the pacemaker 16. Similarly, the pacing lead 31 has an electrode 24 positioned in the right atrium 28 of the heart 18. The lead 31 is thus typically referred to as the atrial lead, and the signals generated by the pacemaker for delivery to the heart through the electrode 24 over lead 31, or the signals sensed through electrode 24 and the lead 31, are processed by circuits in what is known as the atrial channel of the pacemaker 16.

That which is shown in FIG. 1 is a dual-chamber pacemaker. This means that sensing and/or pacing may occur in both chambers of the heart 18, i.e., in the atrium 28 and/or the ventricle 32. The present invention is useful with a dual-chamber pacemaker. However, the basic principles of the invention (sensing and displaying paced and sensed events, including sensed premature ventricular events) could be practiced using a single chamber pacemaker, where sensing and pacing occur in only one chamber, e.g., the ventricle, of the heart. It should also be understood that most pacemakers that provide a dual-chamber configuration, such as is illustrated in FIG. 1, may also be programmed to operate in a single chamber mode.

Figure 2:
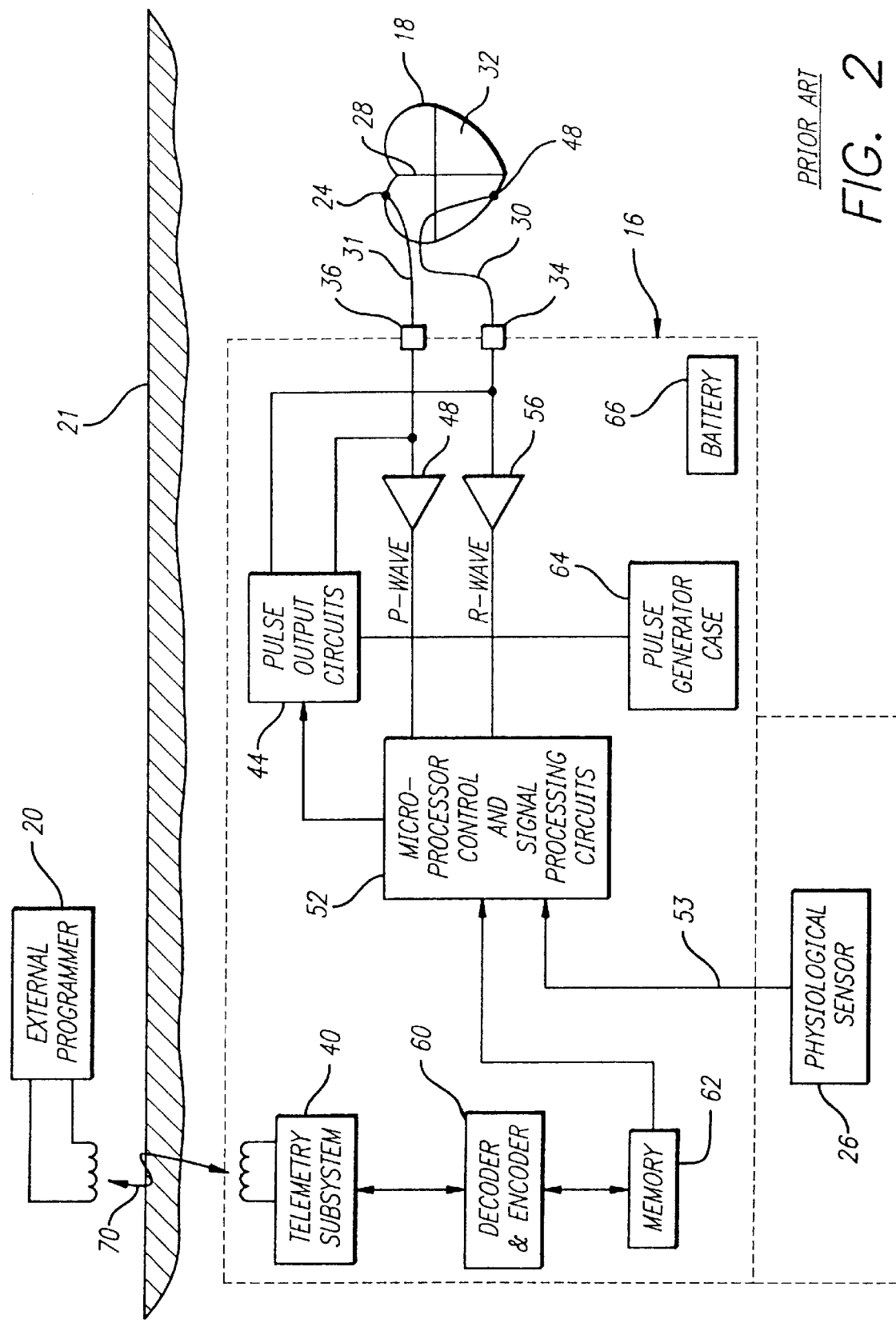
FIG. 2 is a block diagram of a representative implantable pacemaker that may be used with the present invention, and illustrates how an external programmer is used therewith.

Referring next to FIG. 2, a functional block diagram of the dual chamber pacemaker 16 is shown. Note that as shown in FIGS. 1 and 2, the atrial lead 31 and the ventricular lead 30 are unipolar leads. In unipolar operation, the tip electrode 24 or 46 provides one signal path, with the return signal path being provided through conductive body tissue and fluids to an exposed portion of the pacemaker case 64. It is to be understood, however, that either one or both of the leads 30 or 31 could be bipolar leads, having two electrodes, in which case the signal return path is provided through the other electrode (which other electrode is typically a ring electrode that is positioned only a few centimeters from the tip electrode).

As shown in FIG. 2, the pacemaker 16 may be in telecommunicative contact with an external programmer 20 via a telemetry link 70. The programmer 20 includes a telemetry receiver and monitor external to the patient's skin 21. The pacemaker 16 includes a telemetry subsystem 40 for transmitting data and parameter values to the external telemetry transmitter and receiver of the external programmer 20, and for receiving data instructions and the like from the external programmer 20. Data instructions received from the external programmer 20 are decoded in decoder and encoder 60 and stored in memory 62. Likewise, data and parameter values to be sent to the external programmer 20 are encoded in the decoder and encoder circuit 60 prior to transmission. The manner of establishing and operating a telemetry link between an external programmer and implantable medical devices is known in the art.

The data instructions stored in the memory 62 control the operation of the pacemaker. In particular, the stimulation pulses generated by the pacemaker are generated in pulse output circuits 44 as triggered by appropriate trigger signals obtained from a microprocessor control unit 52. The microprocessor control unit 42 defines a plurality of operating states for the pacemaker 16 as a function of various timing signals, also generated by the microprocessor control unit 52, and/or various other signals or conditions sensed through the atrial, ventricular, or telemetry channels of the pacemaker 16. For example, at the conclusion of an appropriate timing interval, typically referred to as the atrial escape interval, control unit 52 changes to a particular state that causes an atrial stimulation pulse (A-pulse) to be generated by the pulse output circuits 44 and delivered to the atrium 28 through the electrode 24 via the atrial lead 31. In a similar manner, the control unit 52 changes to another particular state that causes a ventricular stimulation pulse (V-pulse) to be generated at the conclusion of another timing interval, typically referred to as the ventricular escape interval, which V-pulse is delivered to the ventricle 32 through the electrode 46 via the ventricular lead 30.

When operating in a demand mode, stimulation pulses are provided as above described only in the absence of natural cardiac activity, i.e., only when the heart 18 is not beating (contracting) on its own. Natural cardiac activity is determined by monitoring the leads 30 and/or 31 for electrical activity indicative of muscle contraction. Atrial contraction is manifest by the presence of a P-wave sensed through the atrial tip electrode 24 and the atrial lead 31 through amplifier 48. Similarly, ventricular contraction is manifest by the presence of an R-wave sensed through the ventricular tip electrode 46 and the ventricular lead 30 through amplifier 46. Thus, the occurrence of a P-wave, for example, causes the control unit 52 to immediately assume a different state, which state restarts the atrial escape interval timer (which timer function is carried out by appropriate timer circuits that form part of the microprocessor control unit 52), and thus inhibits an A-pulse from being generated. In like manner, the occurrence of an R-wave causes the control unit 52 to assume yet another state, which state restarts the appropriate time intervals in the pacemaker timer circuits, and inhibits a V-pulse from being generated.

The physiological sensor 26 (usually referred to as just the "sensor"), when used, senses an appropriate physiological parameter, such as physical activity, blood oxygen level, respiration rate, etc. The physiological parameter thus sensed provides some indication of how fast the heart 18 should be beating. That is, in times of high physiological stress, such as a high physical activity level, the heart needs to beat at a much faster rate in order to provide an adequate blood supply to the patient's body. Contrariwise, in times of low physiological stress, such as a very low physical activity level (e.g., when the patient is sleeping), the heart may beat at a much slower rate. Thus, in a pacemaker programmed to operate using the physiological sensor 26, the state logic 42 receives a signal 53 generated by the sensor 26 (generally referred to as the "sensor input signal", because it is the signal that is "input" to the pacemaker 16 from the sensor 26), processes the signal 53 in an appropriate manner, and uses the processed result to alter or adjust the basic time intervals of the pacemaker so that the pacemaker will provide stimulation pulses on demand at a faster or slower rate, as needed. A common type of sensor 26 is an activity sensor, realized using a piezoelectric element that is mounted inside of the case of the pacemaker, which senses the physical activity of the patient.

A pacemaker 16 that is capable of adjusting the rate that stimulation pulses are provided on demand as a function of one or more sensed physiological parameters is known as a "rate-responsive pacemaker." The present invention has applicability to rate-responsive pacemakers, as well as non-rate-responsive pacemakers.

As shown in FIG. 2, the preferred control unit 52 comprises a microprocessor that is controlled by an appropriate programmed set of instructions in the memory 62. Using a microprocessor in this fashion to control a pacemaker is known in the art, as described, e.g., in U.S. Pat. Nos. 5,309,919 (previously incorporated herein by reference). Reference is also made to U.S. Pat. Nos. 4,940,052; 5,431, 691; 5,456,692; and U.S. patent application Ser. No. 08/365, 278, filed Dec. 28, 1994; all of which patents and application are assigned to the same assignee as the present application, and all of which are incorporated herein by reference. The '919, and '692 patents, as well as the 08/365,278 patent application, are particularly relevant for teaching the best mode of implementing a microprocessor-controlled pacemaker, which microprocessor-controlled pacemaker senses, stores and downloads heart rate event data in accordance with the present invention.

The External Programmer

Figure 3:
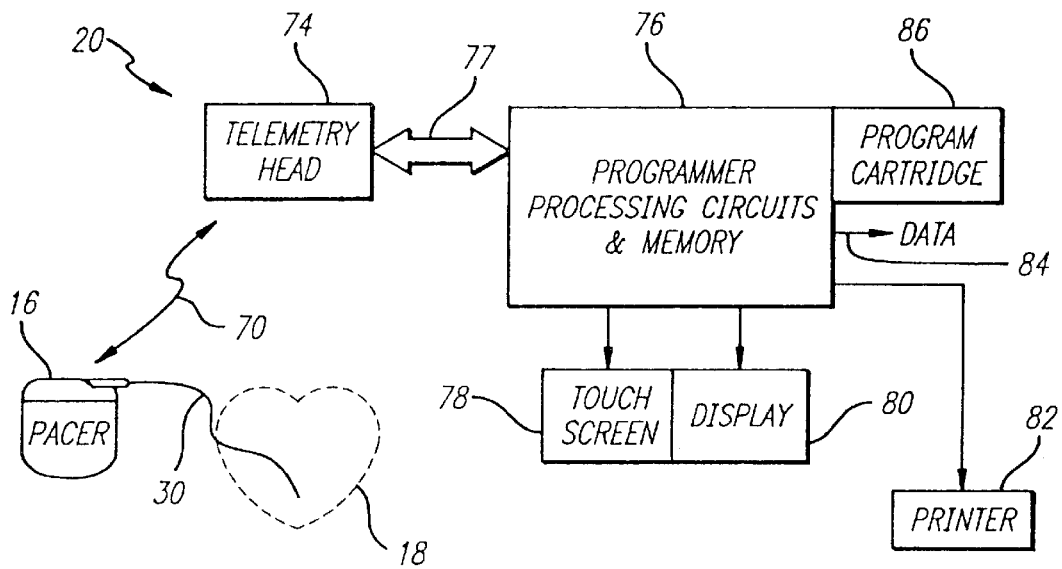
FIG. 3 is a simplified block diagram of an external programmer that may be used with an implantable pacemaker in accordance with the present invention.
Figure 4:
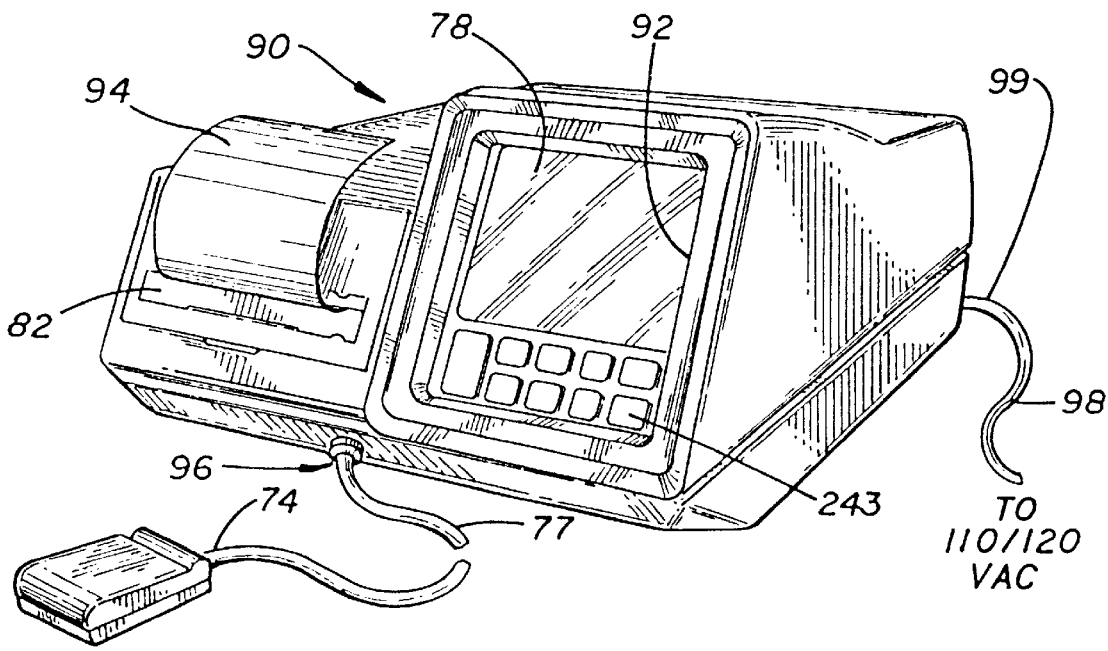
FIG. 4 is a perspective view of the external programmer of FIG. 3.

It is noted that FIGS. 1 and 2, as described above, relate primarily to the pacemaker side of a pacing system 16. However, as noted above, the external programmer side of a pacing system also plays a key part of the invention. It is the external programmer 20 wherein the heart rate/event data is received, processed and displayed (either as an image on a display screen or printed) as a multi-event bin heart rate histogram of the present invention. Hence, a brief overview of the external programmer 20 used with the present invention will next be presented. Such brief overview will be made in connection with FIGS. 3 and 4. FIG. 3 shows a block diagram of an external programmer 20 usable as part of the present invention, while FIG. 4 shows a perspective view of the external programmer of FIG. 3. A more complete description of an external programmer 20 suitable for use with the present invention may be found, e.g., in U.S. Pat. Nos. 4,791,936 and 4,809,697, which patents are also incorporated herein by reference.

The programmer 20 comprises a sophisticated, microprocessor-based programming system that can be used to non-invasively interrogate and program a programmable, implantable pacemaker 16 of the type described above in connection with FIGS. 1 and 2. Because the programmer 20 is itself a microprocessor-based programming system, controlled by program code that may be loaded or inserted therein, any suitable programmer adapted to request and receive heart rate event data from an implantable pacemaker may be configured, or programmed, to prepare the multi-event bin heart rate histograms of the present invention. It is to be understood, therefore, that the description of the programmer that follows is only exemplary and not limiting.

Turning to FIG. 3, a simplified block diagram of the programmer 20 is shown. The programmable pacemaker 16, presumably implanted within living tissue, is in electrical contact with the heart 18 via at least one pacemaker lead 30. (It is noted that while the pacemaker 16 in FIG. 3 is presumed to be implanted in a patient, it need not be implanted for the programmer to function. For example, for training purposes, it is quite common to use a programmer 20 with a non-implanted pacemaker that is coupled to a heart simulator.) As described above in connection with FIGS. 1 and 2, the pacemaker 16 is a self-contained unit capable of both sensing natural cardiac activity (P-waves and/or R-waves) and providing stimulation pulses (A-pulses and/or V-pulses) to invoke paced cardiac activity. The operating characteristics of the pacemaker 16 can be non-invasively programmed by way of command signals received over telemetry link 70, which command signals are received from a telemetry head 74 connected to the programmer processing circuits 76 by way of a connection cable 77. The command signals are generated within the programmer processing circuits 76 as a function of operating commands received by way of a touch sensitive screen 78. That is, a programmer operator selects a desired command by touching a designated area on the touch screen 78, which designated area is defined by a particular pattern displayed on a display screen 80. Advantageously, the touch screen 78 overlays the display screen 80 so that all one need do to make a command selection is to touch the screen at the area indicated on the display for the desired command.

The pacemaker 16 is also capable of sending operating data and measured data over the telemetry link 70 to the telemetry head 74. Such measured data includes heart rate/event data as described more fully below, which heart rate/event data is determined by monitoring particular changes in state of the microprocessor control unit 52. The telemetry head 74 preliminarily processes such data and forwards it on to the programmer processing and memory circuits 76. Data received at the programmer circuits 76 may be displayed on the display screen 80, printed on a printer 82, and/or stored within the memory elements of the programmer circuits 76 for subsequent retrieval and display. Alternatively or conjunctively, rate/event data received at the programmer circuits 76 may be transmitted over an appropriate data channel 84 to a desired external device, such as a modem, an X-Y plotter, a tape or disk drive, a personal computer, or other peripheral device.

Operation of the programmer processing and memory circuits is controlled by way of a program cartridge 86 that is detachably connected to the processing and memory circuits 76. Removable program cartridge 86 thus advantageously allows the operating characteristics of the programmer device to be easily upgraded to include new features and to properly interface with new pacemakers, as new features and new pacemakers are developed. Such upgrading can occur at minimal cost because all that is required is a new program cartridge 86, rather than a whole new analyzer-programming system 20, as has been required in the past. The present invention, relating to a the creation and display of a heart rate histogram with multi-event bins is facilitated through the use of a such new program in a new program cartridge 86.

FIG. 4 illustrates a housing 90 within which the programmer system components are housed. In accordance with one embodiment, all of the circuits of the programmer processing circuits and memory 76, including the printer 82, the display screen 80, the touch screen 78, and the program cartridge 86, are housed within the housing 90. The telemetry head 74 is coupled to the housing 90 by way of cable 77. A CRT screen 92, over which touchscreen 78 is laid, provides a readily visible and accessible means for viewing displays and selecting commands. Similarly, the printer 82 provides a paper copy 94 of that which is displayed on the screen of the CRT 92, or other desired information, as selected by the various commands available through touching the touchscreen. The telemetry head module 74 is attached to cable 77 which plugs into a connector 96 located on the bottom front side of the housing 90. A power cord 98 similarly plugs into socket 99 at the rear of the housing and allows the programmer 20 to be powered from any suitable electrical outlet providing 110 VAC at 60 Hz or other available primary power. The power cord 98 may be stored on the bottom of the housing 90 for ease of transportation and storage. Similarly, the telemetry head 74, when detached, can be stored in a removable front cover (not shown) when not in use.

Gathering the Heart Rate/Event Data

Figure 5:
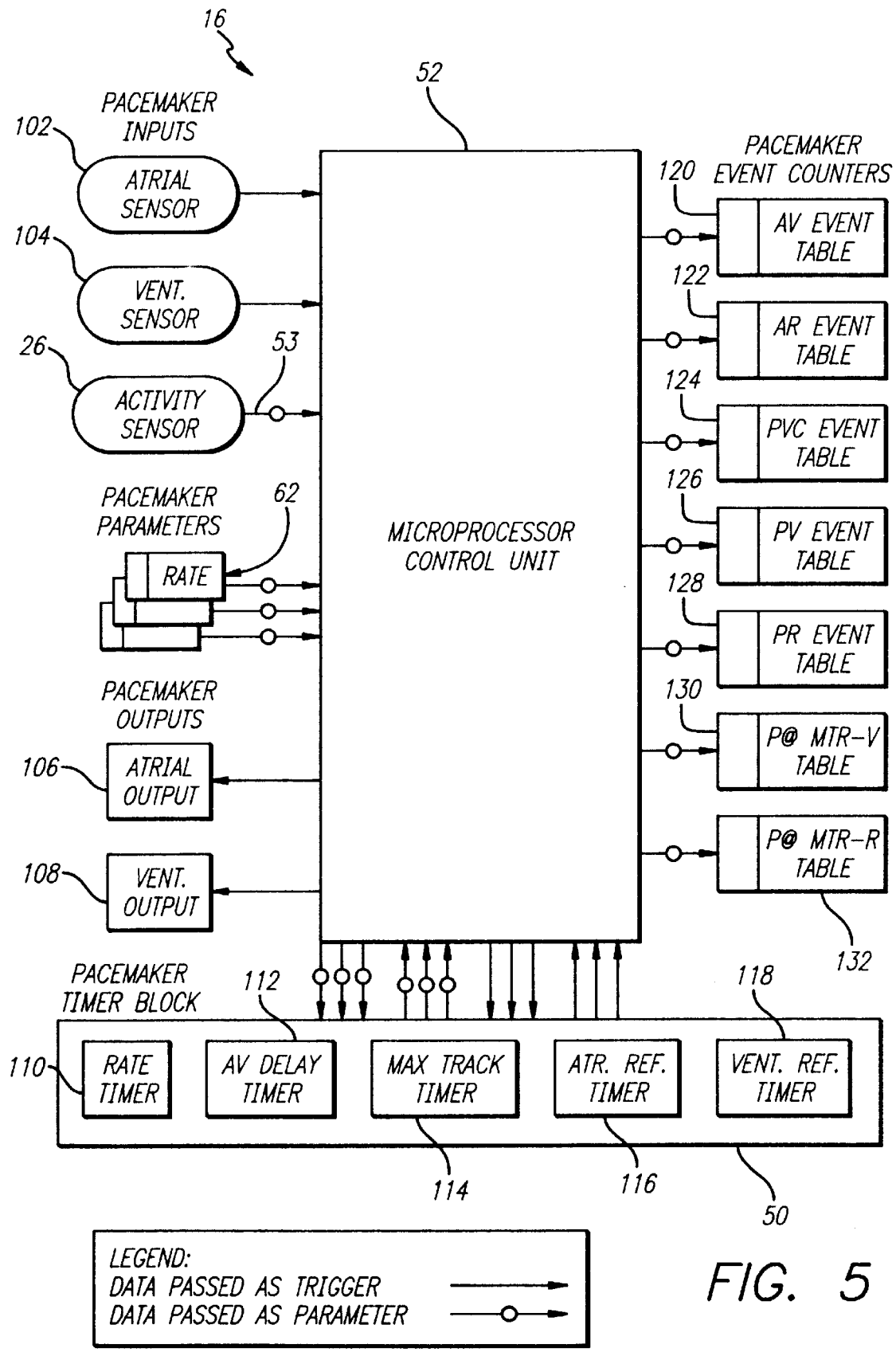
FIG. 5 is a more detailed functional block diagram of the pacemaker of FIG. 2, showing event counters coupled to the microprocessor control unit.

With the above overview in mind of both the pacemaker 16 and the external programmer 20 of a representative pacing system, reference is next made to FIG. 5 where there is shown a more detailed functional block diagram of the pacemaker 16 that highlights the key elements used to gather the heart rate/event data used with the present invention. Shown in FIG. 5 is the microprocessor control unit 52, which microprocessor unit controls the various states and operation of the pacemaker. Also shown in FIG. 5 are the pacemaker timer circuits 50, referred to as the pacemaker timer block. Such timer circuits 50 are actually realized within the microprocessor control unit 52, but are shown separately as the timer block 50 to highlight the separate timing function performed with such circuit. The pacemaker inputs, i.e., signals sensed by the pacemaker that are not programmed, include an atrial sensor 102 and a ventricular sensor 104 that sense P-waves and R-waves, respectively. The pacemaker inputs may also include the sensor input signal 53 obtained from the physiological sensor 26, when used.

In addition to the above-described pacemaker inputs, there are several pacemaker parameters that are input to the pacemaker microprocessor control unit 52 in order to control the operation of the pacemaker in a desired fashion. Such parameters are normally programmed into the memory 62 of the pacemaker 16 using the appropriate telemetry link 70. Such parameters include, e.g., the programmed rate at the which the stimulation pulses are to be generated by the pacemaker, the particular mode of operation of the pacemaker, and the like.

The pacemaker outputs, i.e., signals generated by the microprocessor control unit 52 in response to the pacemaker inputs and/or pacemaker parameters include an atrial output 106 and a ventricular output 108. The atrial output 106 provides an A-pulse for delivery to the atrium at an appropriate time, e.g., on demand as needed to maintain a programmed or sensor-indicated heart rate. The ventricular output 108 similarly provides a V-pulse for delivery to the ventricle at an appropriate time, e.g., on demand as needed to maintain a programmed or sensor-indicated heart rate.

The pacemaker timer circuits 50 include at least five separate timers. A rate timer 110 measures the overall pacing cycle duration. An AV Delay Timer 112 defines the time period between an A-pulse or natural atrial contraction and a V-pulse. A Max Track Timer 114 defines the time period of the maximum rate at which the pacemaker is allowed to provide ventricular stimulation pulses in response to natural atrial contractions, i.e., it defines the maximum tracking rate (MTR). An Atrial Refractory Timer 116 defines the atrial refractory period (i.e., that time period during which the atrial channel is refractory). Similarly, a Ventricular Refractory Timer 118 defines the ventricular refractory period, or that time during which the ventricular channel is refractory.

Typically, there are some eighteen states associated with the operation of the pacemaker 16 when configured for operation in a dual-chamber mode. Three of the eighteen defined states relate directly to cardiac activity that occurs in the atrium. These three atrial states are: (1) atrial pulse (A-pulse); (2) sensed P-wave; and (3) sensed P-wave during the Maximum tracking interval. Similarly, two of the eighteen defined states relate to cardiac activity that occurs in the ventricle. These two ventricle states are: (1) ventricular stimulation pulse (V-pulse); and (2) sensed R-wave. Advantageously, the changing of the state of the microprocessor control unit 52 from one state to another state signals the occurrence of a particular event. Selected state changes associated with the microprocessor control unit 52 may thus be considered as "pacing events". In accordance with the present invention, such "pacing events are recorded as a function of the type of event that occurred, and as a function of the rate of occurrence of such event.

There are multiple pacing event types that are recorded for use by the present invention; the set of applicable events depends on the pacing mode. For dual-chamber modes wherein pacing and sensing occur in both chambers of the heart, e.g., a DDD or DDDR mode, these events are: (1) a P-wave followed by a V-pulse (referred to as a "PV" event); (2) a P-wave followed by an R-wave (referred to as a "PR" event); (3) an A-pulse followed by a V-pulse (referred to as an "AV" event); (4) an A-pulse followed by an R-wave (referred to as an "AR" event); and (5) a premature ventricular event (referred to as a "PVE"). A premature ventricular event, or PVE, is defined as an R-wave that occurs without an appropriate intervening atrial event.

For a VDD mode (wherein pacing only occurs in the ventricle, but sensing occurs in both the atrium and ventricle), the pacing event types that are recorded for use by the invention include: (1) a PV event; (2) a PR event; (3) a V-pulse (also referred to as a "V" event), and (4) a "PVE".

If only single chamber pacing is employed (wherein pacing and sensing occur in just one chamber of the heart), then the pacing events that are counted, and their respective rates, are simply "sensed events" and "paced events".

Because the pacing events defined above are reflected in prescribed state changes of the microprocessor control unit 52, the occurrence of such events may be readily determined by simply monitoring the microprocessor control unit 52 for the prescribed state changes. In particular, in accordance with the present invention, the occurrence of any of the above-defined five pacing events are counted in appropriate pacemaker event counters as a function of rate of occurrence, as shown in FIG. 5. Thus, for example, an AV event table 120 is maintained that keeps track of (i.e., counts) each AV event that occurs. The AV events are tracked in a "table", as opposed to a "counter" because such events are tracked as a function of rate, as well as occurrence. That is, each occurrence of an AV event is logged into the AV event table 120 in an appropriate cell corresponding to the particular frequency or rate of occurrence of the AV event. Thus, the AV event table 120 may be considered as an array of AV event counters, with each counter in the array being assigned a particular rate range, as explained more fully below in connection with FIG. 6.

In a similar manner, an AR event table 122 is maintained to keep track of each AR event that occurs. Likewise, other tables are maintained to keep track of each PVE (table 124), each PV event (table 126), each PR event (table 128), and other events.

Figure 6:
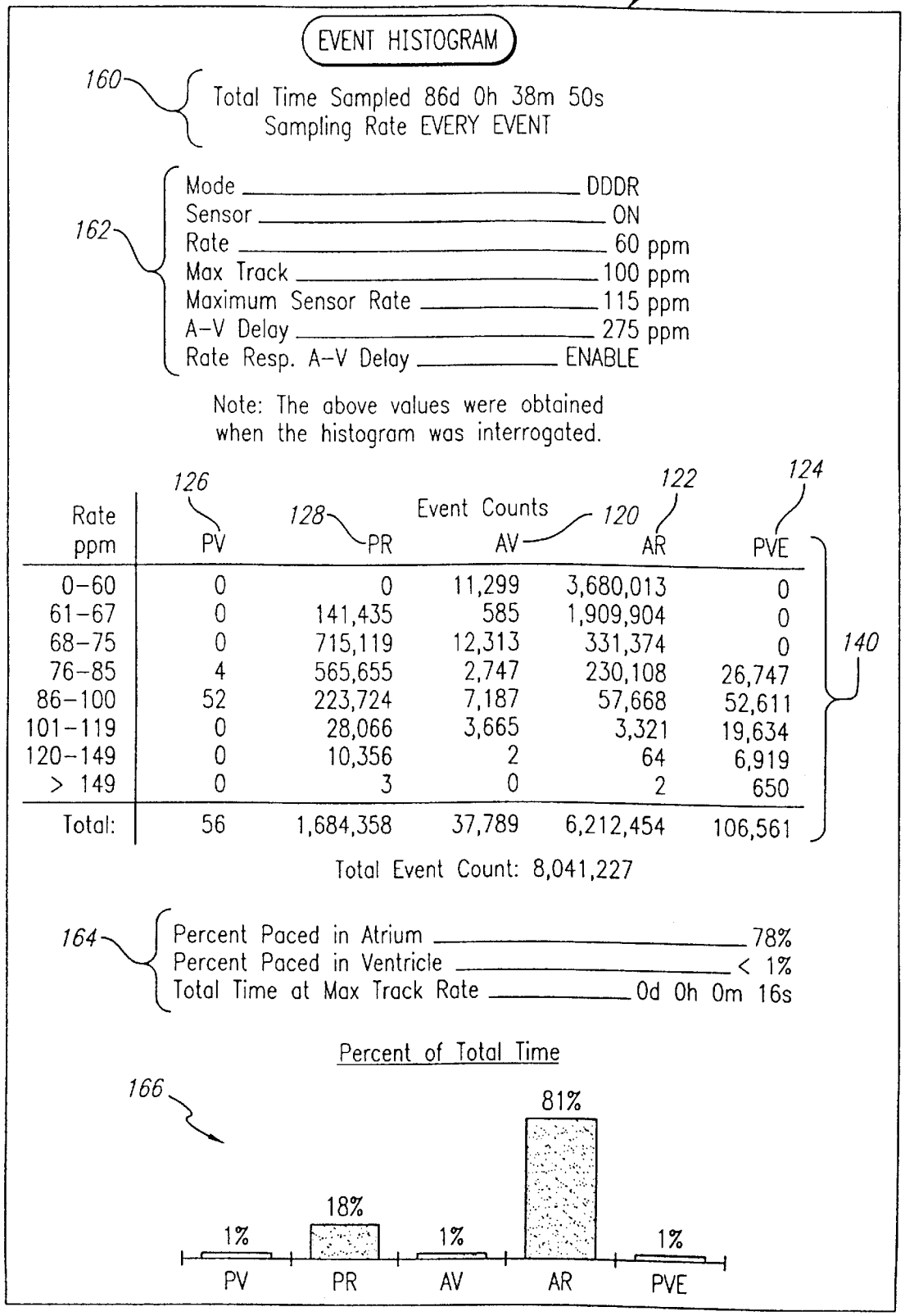
FIG. 6 depicts the type of event histogram data that is conventionally made available to medical personnel through use of the programmer of FIGS. 3 and 4 based on event/rate data gathered by an implantable pacemaker over a substantial time period.

The event tables 120–132 are maintained in the memory 62 of the pacemaker 16. As taught in U.S. Pat. No. 5,309,919, the count data stored in such tables may be organized into an event count table 140 as illustrated in FIG. 6. As seen in FIG. 6, the event count table 140 defines a plurality of rates, expressed as a function of pulses per minute (ppm), along the left side of the event count table. The pacing events being tracked are listed along the top side of the event count table 140. Each column of the event count table 140 shown in FIG. 6 thus corresponds to one of the "event tables" of FIG. 5, and reference numerals have been added at the top of each column in FIG. 6 to show this correspondence.

The other information shown in FIG. 6 along with the event count table 140 represents additional pacing information that could be made available through the programmer 20 to a cardiologist, or other medical personnel, who is monitoring the status and operation of the pacemaker 16. All of this information together is referred to as an "Event Histogram", as seen by the title at the top of FIG. 6. (Note, FIG. 6 conveys essentially the same information as is presented in FIG. 19 of U.S. Pat. No. 5,309,919.) Included in the Event Histogram data is an indication of how long of a time period has elapsed to gather the data shown in the Event Count Table 140. As shown in FIG. 6 at 160, for example, immediately below the title "Event Histogram", the elapsed sampling time for the data shown in FIG. 6 was 86 days (d), zero hours (h), 38 minutes (m), and 50 seconds (s), and the sampling was done on an every event basis. Next, at 162 of FIG. 6, the programmed parameters of the pacemaker are listed. Such parameters include the pacing mode, whether the sensor in "ON" or "OFF", the base pacing rate, the maximum tracking rate, the maximum sensor rate, the AV delay, and whether the rate responsive AV delay is ON or OFF. Then the Event Counts Table 140 is presented, as described above. Based on the data in the Events Count Table, a calculation is then made, with the results printed at 164, as to how much pacing occurred in the atrium, how much occurred in the ventricle, and how much time was spent pacing at the maximum tracking rate of the pacemaker. Also, a bar-graph display 166 is included that shows the percent of total time during which there occurred PV events, PR events, AV events, AR events, or PVE events. For the particular data included in the Event Histogram shown in FIG. 6, it is seen that the vast majority of events (81%) were AR events, and most of the rest of the events (18%) were PR events. Such information is helpful to the cardiologist, or other medical personnel, as they evaluate the performance of the pacemaker 16 for the particular patient within whom it has been implanted.

Heart Rate Histogram with Multi-Event Bins

While the information included in the Event Histogram printout of the type shown in FIG. 6 is extremely useful to medical personnel as they evaluate the performance of a pacemaker implanted in a given patient, such information falls short in providing such personnel with a quick, easy-to-understand overview of exactly what types of events are happening at which heart rates. To overcome this difficulty, the present invention improves the manner in which the heart rate event data included in the event count table 140 is graphically presented.

Figure 7:
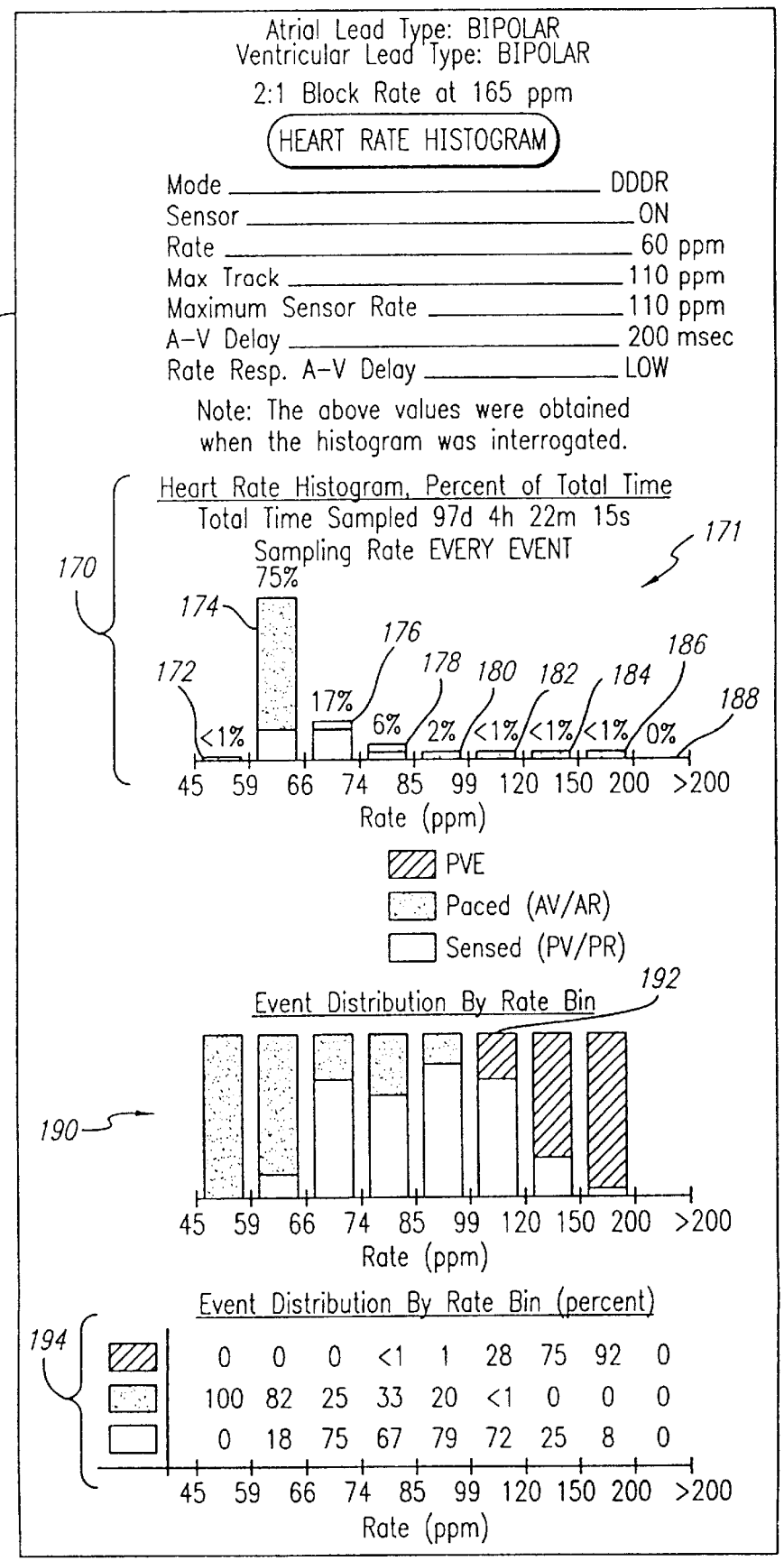
FIG. 7 depicts the type of heart rate histogram data, including two embodiments of a multi-event bin heart rate histogram, that are made available to medical personnel through use of the programmer of FIGS. 3 and 4, or equivalent data receiving and processing device, in accordance with the present invention.
Figure 8:
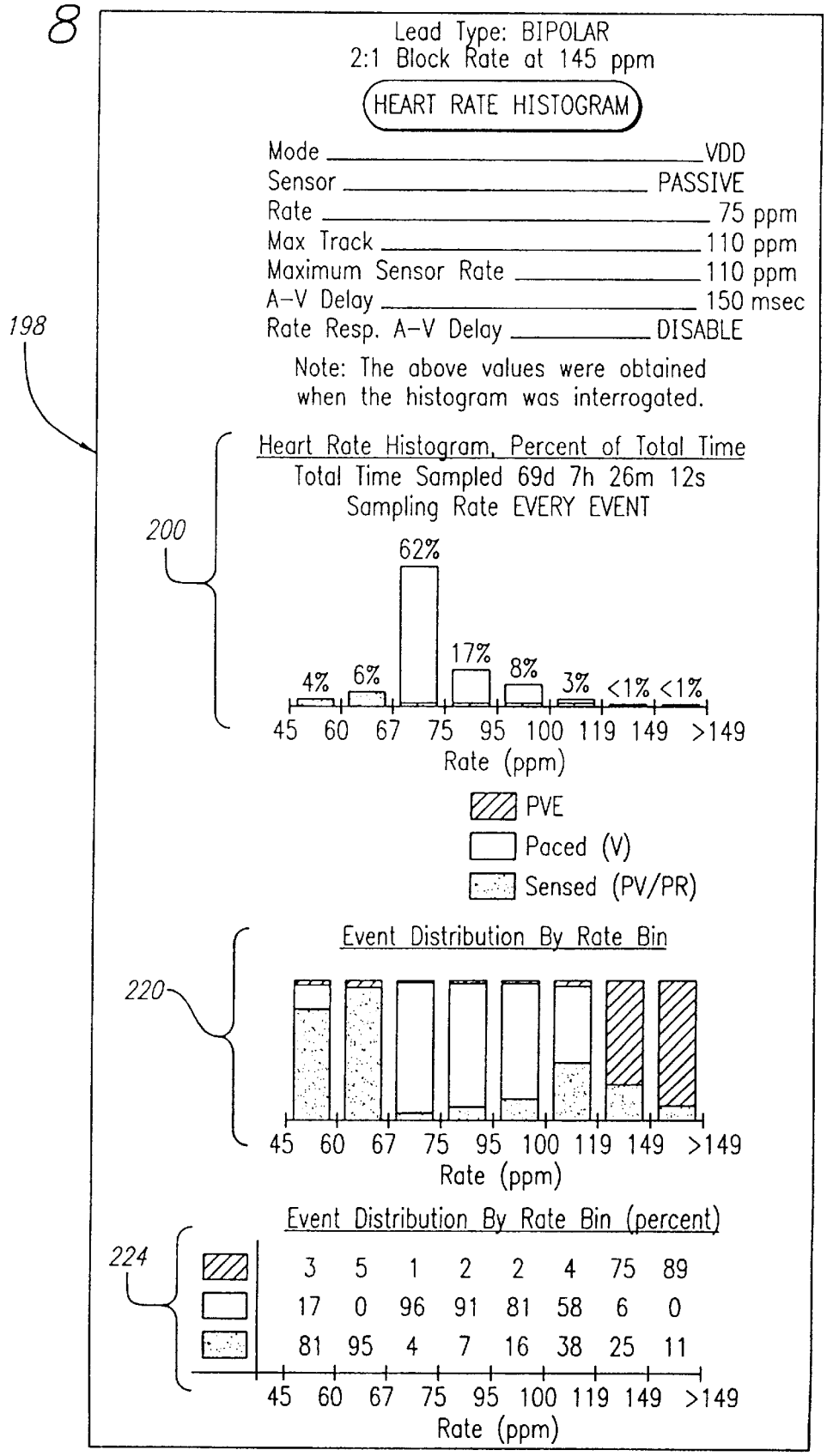
FIG. 8 depicts a variation of the multi-event bin heart rate histogram of the present invention used, e.g., for VDD pacing.

More particularly, the present invention creates two different types of multi-event bin heart rate histograms as shown in FIGS. 7 and 8. Such multi-event bin heart rate histograms, once the need for such histograms has been identified and specified, as presented herein, may be compiled from the data in the event count table 140 using conventional programming techniques known to those of skill in the art. There are two types of heart rate histograms shown in each of FIGS. 7 and 8. Each type of heart rate histogram thus shown in FIGS. 7 and 8 is a multi-event bin histogram. This means that multi-event data is included, or graphically depicted, within each bin of each histogram. More particularly, each bin of each histogram shows whether the events that occurred at the rate of that particular bin included a "paced" event (which includes AV or AR events for the histograms shown in FIG. 7; and includes V events for the histograms shown in FIG. 8), a "sensed" event (which includes PV or PR events for both FIGS. 7 and 8), or a premature ventricular event ("PVE").

Referring first to FIG. 7, which shows the multi-event bin heart rate histograms of the present invention as obtained from a DDDR pacing mode, a first type of multi-event bin heart rate histogram is shown at 170 in FIG. 7. As seen in FIG. 7, the multi-event bin heart rate histogram 170 comprises a two-dimensional graphical chart 171 of the heart rate event data. The chart 171 includes a multiplicity of heart rate zones (or bins), e.g., nine rate bins, arranged in order of increasing heart rate along a first axis, e.g., along the horizontal axis. Thus, as seen in FIG. 7, from left to right, there is a first rate bin 172 for the 45–59 ppm rate zone, a second rate bin 174 for the 60–66 ppm rate zone, a third rate bin 176 for the 67–74 ppm rate zone, a fourth rate bin 178 for the 75–85 ppm rate zone, a fifth rate bin 180 for the 86–99 ppm rate zone, a sixth rate bin 182 for the 100–120 ppm rate zone, a seventh rate bin 184 for the 121–150 ppm rate zone, an eighth rate bin 186 for the 151–200 ppm rate zone, and a ninth rate bin 188 for the >200 ppm rate zone.

The chart 171 also includes a graphical representation of the number of heart rate events that occur within each heart rate zone, or bin. While many different types of graphic representations could be used for this purpose, that used in FIG. 7 is simply a vertical display bar for each bin that extends upwards by an amount indicative of the relative number of events, or event counts, that have occurred within the bin. Thus, for example, for the particular heart rate event data shown in FIG. 7, most (75%) of the events have occurred in the second rate bin 174, and thus the vertical bar for rate bin 174 extends up much higher than any of the other bars for the other rate bins. A significant number of events (17%) also occurred in the third rate bin 176, and thus the vertical bar for rate bin 176 extends up almost one quarter of the height of the second bin 174 (because 17% is roughly 23%—almost ¼—of 75%). It is noted that while FIG. 7 shows the chart 171 with the display bars being vertical bars, and the rate bins distributed along the horizontal axis, there is no reason why the display bars could not be made horizontal bars, with the distribution of rate bins (or zones) occurring along the vertical axis.

Most importantly for purposes of the present invention, as also evident from FIG. 7, the multi-event bin chart 171 further includes an indication of which events in each heart rate zone or bin are sensed events, which are paced events, and which are premature events. Such indication is made by segmenting the display bars of each rate bin into first, second and third portions. A first portion, shown, e.g., as a black or filled portion of the display bar, has a segment length that represents the number of paced events (e.g., AV or AR events) that have occurred within the corresponding heart rate bin. A second portion, shown, e.g., as a white or non-filled portion of the display bar, has a segment length that represents the number of sensed events that have occurred within the corresponding heart rate bin. A third portion, shown, e.g., as a gray or partially-filled portion of the display bar, has a segment length that represents the number of premature events, or PVE's, that have occurred within the corresponding heart rate bin. (For the data included in the chart 171 of FIG. 7, the number of premature events that have occurred is so few that such a gray or partially-filled portion is not readily discernable.) In this manner, each rate bin of the heart rate histogram thus displays the relative occurrence of multiple events that have occurred at the rate zone corresponding to that bin. In other words, the bins of the histogram comprise multi-event bins where the relative occurrence of multiple events, e.g., paced, sensed, or PVE events, at that rate can be quickly and easily seen with just a glance at the histogram.

It is to be emphasized that while only three types of events are depicted in the heart rate histogram 170 shown in FIG. 7, such is only exemplary. Any number of event types could be displayed as separate segments of the respective display bars. For purposes of the present invention, however, the three events displayed—paced events, sensed events, and PVE's—have been found to be sufficient for readily conveying to the medical personnel all of the information needed to make a quick and accurate assessment of the pacemaker's performance.

Note that the multi-event bin histogram 170 in FIG. 7 also includes an indication of the total sampling time during which the heart rate event data was gathered by the implantable pacemaker. For the data shown in FIG. 7, this sampling time is "97 d 4 h 22 m 15 s", or 97 days, 4 hours, 22 minutes and 15 seconds.

The type of multi-event bin heart rate histogram shown at 170 in FIG. 7 depicts the events as a percent of total time, or total events. The total length of all of the display bars used in each rate bin thus represents 100% of all the heart rate events that have occurred. Thus, where 75% of the events occurred at the rate defined by the second rate bin 174, the display bar for rate bin 174 is the longest (or highest) of all of the display bars. Similarly, where 17% of the events occurred at the rate defined by the third rate bin 176, the display bar for rate bin 176 is just a little less than ¼ as long (or high) as the display bar for rate bin 174. Likewise, where 6% of the events occurred at the rate defined by the fourth rate bin 178, the display bar for rate bin 178 is about ⅓ the length (or height) as the display bar for rate bin 176.

The percent-of-total-time format used for the multi-event bin heart rate histogram 170 of FIG. 7 necessarily limits the amount of useful information that can be gleaned from those rate bins wherein the number of occurrences is low, e.g., less than 1 or 2%. The display bars for rate bins 182, 184 and 186, for example, where the events that occurred were less than 1%, do not convey any meaningful information relative to the distribution of events within these rate zones (or bins). Further, because the number of PVE events in each of the rate bins is few, if any, it is impossible to discern how many PVE's occurred in any given rate bin.

To overcome the above deficiencies, the present invention provides a second type of multi-event bin heart rate histogram as is shown at 190 in FIG. 7. This second type of histogram 190 shows the distribution of events within each bin, or rate zone, regardless of the number of events that occurred within such bin. As seen in FIG. 7, each display bar for each heart rate bin of the histogram 190 is of the same length. The length of the display bar represents 100% of the number of heart rate events that have occurred within the respective heart rate bin. The multiple events that occur within each heart rate bin, or zone, are then displayed by segmenting the display bar into however many multiple event types are being displayed. Thus, where three types of events are of interest—paced events, sensed events, and PVE's—the fixed-length display bar of each rate bin is divided into three segments. The segments are uniquely identified in the same manner as used for the histogram 170, i.e., sensed events are shown by a non-filled or white segment, paced events are shown by a completely-filled or black segment, and PVE's are shown by a partially-filled (or dotted, or cross-hatched) segment. The segment that corresponds to sensed events has a segment length corresponding to the number of sensed events that have occurred within that heart rate zone as compared with all of the heart rate events that have occurred in that corresponding heart rate zone. For example, 72% of the events that occurred in the seventh rate bin 192 (corresponding to the rate range of 100–120 ppm) of histogram 190 in FIG. 7 were sensed events (PV or PR events), while less than 1% were paced events, and 28% were PVE's. (This quantitative percentage data is obtained from the "Event Distribution By Rate Bin (percent)" table 194 which appears immediately below the histogram 190 in FIG. 7.) Thus, the event bar of bin 192 is segmented into three portions. A first portion, corresponding to sensed events, has a length that is approximately 72% of the total length of the display bar. Similarly, a second portion, corresponding to paced events, has a length that is approximately 1% of the total length of the display bar; while a third portion, corresponding to PVE's, has a length that is approximately 28% of the total length of the display bar. The display bars for the other rate bins are segmented in a similar manner, with each segment length of each rate bin representing the percentage of occurrences of the particular event of interest (sensed, paced, or PVE) within that rate bin relative to 100% of the events that occurred in that particular rate bin.

By using a heart rate histogram 190 as thus described, it is thus possible for medical personnel to quickly see at just a glance the distribution of events that occur within each rate bin, even though the total events within the rate bin may be a very small percentage of the total events that have occurred in all of the heart rate bins. For example, as seen in the histogram 170, the number of events that occurred in the rate bin 182 corresponding to 100–120 ppm was less than 1% of the total events included in the sample size. Nonetheless, the histogram 190 breaks this less-than-1% data down and shows roughly that 75% of these events were sensed events, less than 1% were paced events, and 28% were PVE's. Such information, showing the distribution of events within each heart rate bin, represents extremely valuable information for the medical personnel who are monitoring the performance of the pacemaker for a given patient. The histogram 190 advantageously conveys this distribution event data quickly and qualitatively, while the event distribution table 194 below the histogram 190 (FIG. 7) presents the same information quantitatively.

Referring next to FIG. 8, two additional heart rate histograms 200 and 220 are illustrated to depict the event/rate data in a multi-event bin rate histogram format for event/rate data obtained while pacing in the VDD mode. The total sampling time over which the VDD event/rate data was obtained was 69 days, 7 hours, 26 minutes and 12 seconds, as indicated just below the title of the histogram 200. The histograms 200 and 220 of FIG. 8 are formatted the same as the histograms 170 and 190 described above in connection with FIG. 7, except that only eight rate bins are used, rather than the nine rate bins of FIG. 7.

For example, referring to the multi-event bin rate histogram 200 of FIG. 8, it is seen that the events are depicted as a percent of total time, or total events as vertical, segmented, display bars, with each bar corresponding to a rate bin. For the format used in FIG. 8, eight rate bins are used. A first rate bin 202 corresponds to the 45–60 ppm rate zone, a second rate bin 204 corresponds to the 61–67 ppm rate zone, a third rate bin 206 corresponds to the 68–75 ppm rate zone, a fourth rate bin 208 corresponds to the 76–85 ppm rate zone, a fifth rate bin 210 corresponds to the 86–100 ppm rate zone, a sixth rate bin 212 corresponds to the 100–120 ppm rate zone, a seventh rate bin 214 corresponds to the 121–149 ppm rate zone, and an eighth rate bin 216 corresponds to the >149 ppm rate zone.

The multi-event bin rate histograms 200 and 220 of FIG. 8 (corresponding to a VDD mode of operation of the pacemaker) further differ from the histograms 170 and 190 of FIG. 7 (which correspond to a DDDR mode of operation) in that sensed events in FIG. 8 (comprising either PV or PR events) are depicted using a black or filled segment of the display bar, and paced events (comprising a "V" event) are depicted as a white or non-filled segment of the display bar. Such representation in FIG. 8 of which segments represent paced events and which represent sensed events is reversed from that used in FIG. 7 to highlight that the multi-event bin rate histograms thus displayed correspond to a different mode of operation of the pacemaker.

Other than the number of rate bins and the reversal of the representation of paced and sensed events, the multi-event bin rate histograms of FIGS. 7 and 8 are the same, and the description above of the histograms 170 and 190, and the table 194, in connection with FIG. 7 applies equally well to the histograms 200 and 220, and the table 221, of FIG. 8. It is to be emphasized that the present invention is not limited to the particular formats used for the multi-event bin rate histograms shown in FIGS. 7 and 8, but applies to any type of multi-event bin rate histogram of the general type shown in FIGS. 7 and 8, regardless of the number of rate bins employed, the range of ppm assigned to each rate bin, or the type of graphical marking (black, white, gray, colored, cross-hatched, dotted, etc.) used to mark one type of event segment from another within each rate bin.

Figure 9:
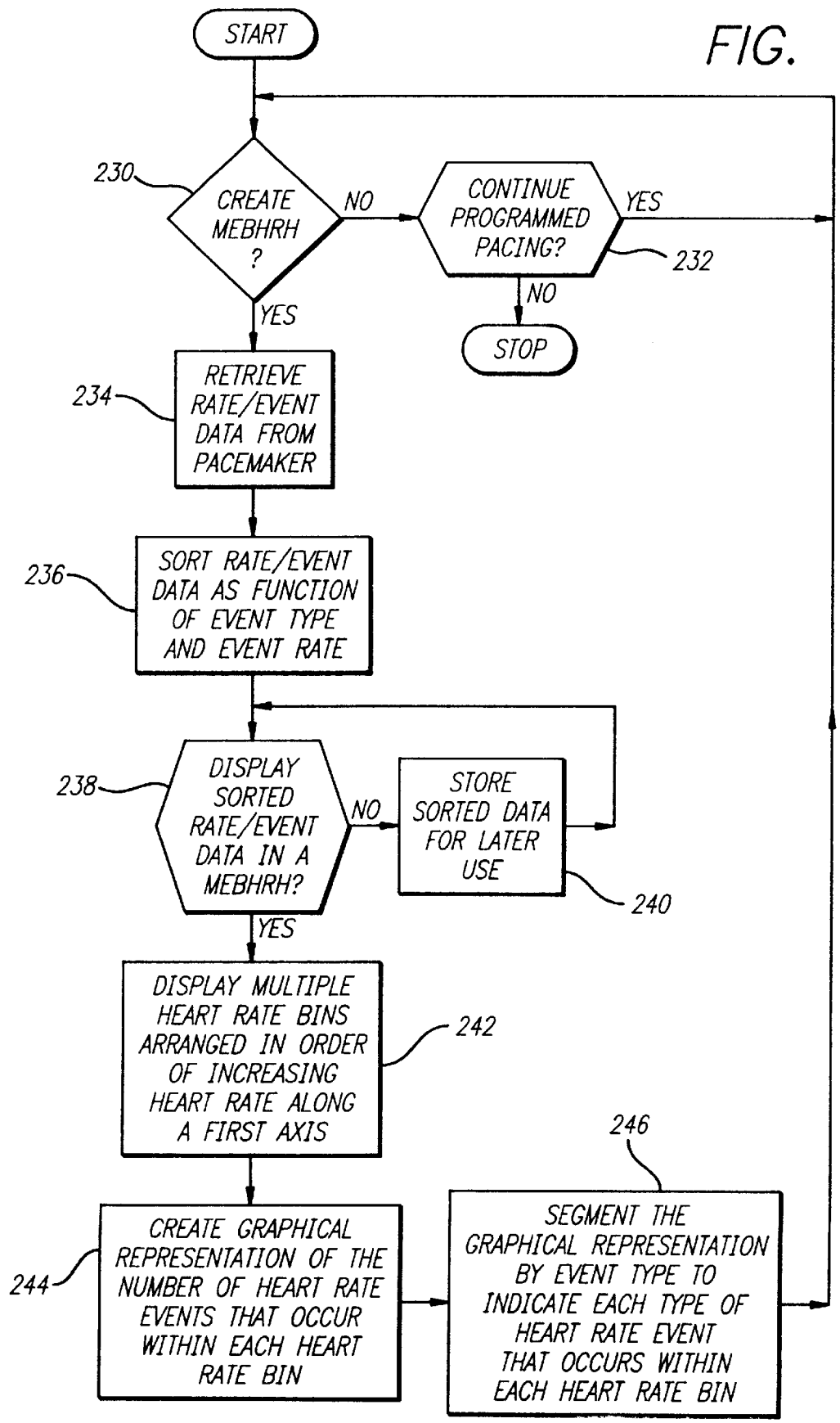
FIG. 9 is a flowchart of the method used by the present invention for displaying a multi-event bin heart rate histogram.

A flowchart showing the method used by the present invention to create a multi-event bin heart rate histogram is shown in FIG. 9. It is noted that the flowchart shown in FIG. 9 is a simplified flowchart in that it depicts only the main method steps used to create a multi-event bin heart rate histogram (MEBHRH) in accordance with the present invention. As is known by those of skill in the art, particularly those who write the operating code and programs for implanted pacemakers and programmers, there are many additional details and steps related to the operation of a pacing system which are not shown in FIG. 9, but which do not relate directly to the present invention. Hence, such details are not included in FIG. 9.

As seen in FIG. 9, if a decision is made to create the MEBHRH (YES branch of block 230), then the rate/event data is retrieved from the pacemaker (block 234). If a decision is made not to create the MEBHRH (NO branch of block 230), and if the pacemaker is to continue its pacing operation in accordance with its programmed mode (YES branch of block 232), then such programmed pacing continues until a decision is made to either stop pacing (NO branch of block 232, which could include changing the programmed mode of operation) or to create the MEBHRH (YES branch on block 230). Such programmed pacing would include, e.g., continuing to gather and store the event histogram data as described in U.S. Pat. No. 5,309,919.

Once the event/rate data has been retrieved, it is sorted as a function of event type and event rate (block 236). If such sorted data is not to be displayed in a MEBHRH (NO branch of block 238), then such sorted data may be stored for later use (block 240). If, however, the sorted event/rate data is to be displayed in a MEBHRH (YES branch of block 238), then multiple heart rate bins are defined and arranged in order to increasing heart rate along a first axis of the MEBHRH display (block 242). For example, as shown in FIG. 7, nine heart rate bins may be displayed, or as shown in FIG. 8, eight heart rate bins may be displayed.

Next, a graphical representation of the number of heart rate events that occur within each heart rate bin is created (block 244). For example, such graphical representation may be a vertical bar of variable length as shown for the "Percent of Total Time" histograms 170 (FIG. 7) or 200 (FIG. 8); or may be a vertical bar of fixed length as shown for the "Event Distribution By Rate Bin" histograms 190 (FIG. 7) or 220 (FIG. 8).

Finally, the graphical representation created (in block 244) is segmented by event type (block 246) in order to indicate each type of heart rate event that has occurred within each heart rate bin. For example, if three event types are to be shown within each heart rate bin, the vertical bars shown in FIGS. 7 or 8 are segmented with white (or non-filled) portions, black (or filled) portions, and/or gray (dotted, cross-hatched, etc.) portions, with each portion thus marked presenting a graphical indication of the relative number of that particular event type that has occurred within that rate bin.

As described above, it is thus seen that the present invention displays event/rate data gathered by an implantable pacemaker in an easy-to-understand graphical representation. More particularly, the invention provides two types of heart rate histograms having multiple event bins. In a first, the number of occurrences of multiple events in each heart rate zone, or bin, is displayed as a function of the total number of occurrences at all rates. In a second, the distribution of the number of occurrences of multiple events in each heart rate zone, or bin, is conveyed regardless of the total number of occurrences within that bin.

Through use of the multi-event bin heart rate histogram(s) of the present invention, the heart rate/event data is presented in a way that enables an attending physician (or other medical personnel), with just a glance or two at the histogram(s), to quickly and easily comprehend the performance of the pacemaker and its interaction with the patient. In turn, such information thereafter serves to guide the attending medical personnel to the most effective pacemaker therapy for the patient as the pacemaker is monitored, programmed and/or reprogrammed.

While the invention herein disclosed has been described by means of specific embodiments and applications thereof, numerous modifications and variations could be made thereto by those skilled in the art without departing from the scope of the invention set forth in the claims.

What is claimed is:

1. A pacing system comprising:

an implantable pacemaker having means for sensing and recording heart rate/event data, means responsive to receipt of a download request signal for downloading the heart rate/event data to a remote receiver, and means for receiving the download request signal; and an external programmer comprising:

means for generating the download request signal and sending it to the implantable pacemaker, means for receiving the heart rate/event data from the implantable pacemaker, and means for displaying the heart rate/event data in a multi-event bin heart rate histogram;

the multi-event bin heart rate histogram comprising a two-dimensional graphical chart of the heart rate/event data that shows: (a) a multiplicity of heart rate zones arranged in order of increasing heart rate along a first axis, (b) a graphic representation of the number of heart rate events that occur within each heart rate zone, and (c) an indication of which events in each heart rate zone are sensed events, which are paced events, and which are premature events.

2. The pacing system, as set forth in claim 1, wherein:

the graphic representation of the number of heart rate events that occur within each heart rate zone comprises a display bar for each heart rate zone that extends out from the first axis, and the display bar for each heart rate zone has a length that is indicative of the total number of heart rate events that occur within the respective heart rate zone.

3. The pacing system, as set forth in claim 1, the graphic representation comprises a display bar for each heart rate zone that extends out from the first axis, wherein the display bar of each heart rate zone is segmented into first, second and third portions, and wherein:

the first portion has a segment length that represents the number of sensed events that have occurred within the corresponding heart rate zone, the second portion has a segment length that represents the number of paced events that have occurred within the corresponding heart rate zone, and the third portion has a segment length that represents the number of premature events that have occurred within the corresponding heart rate zone.

4. The pacing system, as set forth in claim 2, wherein the multi-event heart rate histogram further comprises an indication of the percent of the total events associated with each heart rate zone as compared to the total heart rate events from all of the heart rate zones.

5. The pacing system, as set forth in claim 1, wherein:

the graphic representation of the number of heart rate events that occur within each heart rate zone comprises a display bar for each heart rate zone that extends out from the first axis, the display bar for each heart rate zone has a length that is representative of 100% of the number of heart rate events that have occurred within the respective heart rate zone, the display bar of each heart rate zone is segmented into a plurality of portions, the plurality of portions including:

a first portion having a segment length indicative of the number of sensed events that have occurred within the corresponding heart rate zone as compared with all of the heart rate events that have occurred in that corresponding heart rate zone, and a second portion having a segment length indicative of the number of paced events that have occurred within the corresponding heart rate zone as compared with all of the heart rate events that have occurred in that corresponding heart rate zone, whereby the heart rate histogram provides a graphical indication of the heart rate event distribution by rate zone.

6. The pacing system, as set forth in claim 5, wherein the display bar of each heart rate zone further includes a third portion having a segment length indicative of the number of premature events that have occurred within the corresponding heart rate zone as compared with all of the heart rate events that have occurred in that corresponding heart rate zone.

7. The pacing system of claim 6, wherein the multi-event heart rate histogram further comprises an event-distribution-by-rate-zone table which displays the percentage of each heart rate event type within each heart rate zone, where the heart rate event types include sensed events, paced events, and premature events.

8. The pacing system of claim 1, wherein the implantable pacemaker comprises a dual-chamber pacemaker capable of sensing and pacing in both atrial and ventricular chambers, and wherein the heart rate event data sensed and recorded by the pacemaker includes: (1) a P-wave followed by a V-pulse (referred to as a "PV" event); (2) a P-wave followed by an R-wave (referred to as a "PR" event); (3) an A-pulse followed by a V-pulse (referred to as an "AV" event); (4) an A-pulse followed by an R-wave (referred to as an "AR" event); and a premature ventricular event (referred to as a "PVE"), and further wherein all PV and PR events are considered to be sensed events, all AV and AR events are considered to be paced events, and all PVE events are considered to be premature events.

9. The pacing system of claim 1, wherein the implantable pacemaker comprises a dual-chamber pacemaker capable of sensing in both atrial and ventricular chambers, but capable of pacing in only the ventricular chamber, and wherein the heart rate event data sensed and recorded by the pacemaker includes: (1) a P-wave followed by a V-pulse (referred to as a "PV" event); (2) a P-wave followed by an R-wave (referred to as a "PR" event); (3) a V-pulse (referred to as a "V" event) and (4) a premature ventricular event (referred to as a "PVE"), and further wherein all PV and PR events are considered to be sensed events, all V events are considered to be paced events, and all PVE events are considered to be premature events.

10. The pacing system of claim 1, wherein the implantable pacemaker comprises a single-chamber pacemaker capable of sensing and pacing in just one heart chamber, and wherein the heart rate event data sensed and recorded by the pacemaker includes: (1) a sensed event (a P-wave or an R-wave, depending upon which heart chamber is being used); and (2) a paced event (an A-pulse or a V-pulse, depending upon which heart chamber is being used).

11. An external programmer for use with an implantable pacemaker, the implantable pacemaker having means for sensing and recording heart rate event data, means responsive to receipt of an event data request signal for transferring the heart rate event data to the programmer, and means for receiving the event data request signal, said external programmer comprising:

means for generating the event data request signal and sending it to the implantable pacemaker;

means for receiving the heart rate event data from the implantable pacemaker; and means for displaying the heart rate event data in a multi-event bin heart rate histogram, the multi-event bin heart rate histogram comprising a graphical chart of the heart rate event data that shows:
a multiplicity of heart rate bins arranged in order of increasing heart rate along a first axis,
a graphical representation of the number of heart rate events that occur within each heart rate bin, and
an indication of at least three types of heart rate events in each heart rate bin.

12. The external programmer, as set forth in claim 11, wherein:
the graphic representation of the number of heart rate events that occur within each heart rate bin comprises a display bar for each heart rate bin that extends out from the first axis, and
the length of the display bar for each heart rate bin is indicative of the total number of heart rate events that occur within the respective heart rate bin.

13. The external programmer, as set forth in claim 12, wherein the display bar of each heart rate bin is divided into a plurality of segments, with each segment having a length that represents the number of occurrences of a specific type of heart rate event within the corresponding heart rate bin.

14. The external programmer, as set forth in claim 13, wherein the multi-event bin heart rate histogram further provides an indication of the percent of the total events associated with each heart rate bin as compared to the total heart rate events from all of the heart rate bins.

15. The external programmer, as set forth in claim 13, wherein at least two of the at least three types of heart rate events that may be identified in each heart rate bin of the multi-event bin heart rate histogram comprise sensed events and paced events.

16. The external programmer, as set forth in claim 15, wherein at least one of the at least three types of heart rate events that may be identified in each heart rate bin of the multi-event bin heart rate histogram further comprise premature events.

17. The external programmer, as set forth in claim 16, wherein the implantable pacemaker comprises a dual-chamber pacemaker that includes means for sensing P-waves and R-waves, means for generating A-pulses and V-pulses, and means for sensing a premature ventricular event (PVE); and further wherein the specific types of heart rate events that may be identified in each heart rate bin of the multi-event bin heart rate histogram comprise: (1) a P-wave followed by a V-pulse (referred to as a "PV" event); (2) a P-wave followed by an R-wave (referred to as a "PR" event); (3) an A-pulse followed by a V-pulse (referred to as an "AV" event); (4) an A-pulse followed by an R-wave (referred to as an "AR" event); and (5) a PVE; and further wherein all PV and PR events are considered to be sensed events, all AV and AR events are considered to be paced events, and all PVE events are considered to be premature events.

18. The external programmer, as set forth in claim 16, wherein the implantable pacemaker comprises a dual-chamber pacemaker that includes means for sensing P-waves and R-waves, means for generating V-pulses and means for sensing a premature ventricular event (PVE); and further wherein the specific types of heart rate events that may be identified in each heart rate bin of the multi-event bin heart rate histogram comprise: (1) a P-wave followed by a V-pulse (referred to as a "PV" event); (2) a P-wave followed by an R-wave (referred to as a "PR" event); (3) a V-pulse (referred to as a "V" event); and (4) a PVE; and further wherein all PV and PR events are considered to be sensed events, all V events are considered to be paced events, and all PVE events are considered to be premature events.

19. The external programmer, as set forth in claim 15, wherein the implantable pacemaker comprises a single-chamber pacemaker that includes means for sensing P-waves or R-waves, and means for generating A-pulses or V-pulses, depending upon which heart chamber is used; and further wherein the specific types of heart rate events that may be identified in each heart rate bin of the multi-event bin heart rate histogram comprise: (1) a P-wave or R-wave; and (2) an A-pulse or a V-pulse; and further wherein all P-waves or R-waves are considered to be sensed events, and all A-pulses or V-pulses are considered to be paced events.

20. The external programmer, as set forth in claim 11, wherein:
the graphical representation of the number of heart rate events that occur within each heart rate bin comprises a display bar for each heart rate bin that extends out from the first axis,
the display bar for each heart rate bin has a length that is representative of 100% of the number of heart rate events that have occurred within the respective heart rate bin, and
the display bar of each heart rate bin is divided into a plurality of segments, with each segment having a length indicative of the number of occurrences of a specific type of heart rate event within the corresponding heart rate bin as compared with all of the occurrences of all of the heart rate events in that corresponding heart rate bin;
whereby the heart rate histogram provides a graphical indication of the heart rate event distribution by rate bin.

21. The external programmer, as set forth in claim 20, wherein the specific types of heart rate events that may be identified in each heart rate bin of the multi-event bin heart rate histogram comprise sensed events and paced events.

22. The external programmer, as set forth in claim 21, wherein the implantable pacemaker comprises a single-chamber pacemaker that includes means for sensing P-waves or R-waves, and means for generating A-pulses or V-pulses, depending upon which heart chamber is used; and further wherein the specific types of heart rate events that may be identified in each heart rate bin of the multi-event bin heart rate histogram comprise: (1) a P-wave or R-wave; and (2) an A-pulse or a V-pulse; and further wherein all P-waves or R-waves are considered to be sensed events, and all A-pulses or V-pulses are considered to be paced events.

23. The external programmer, as set forth in claim 21, wherein the specific types of heart rate events that may be identified in each heart rate bin of the multi-event bin heart rate histogram further comprise premature events.

24. The external programmer, as set forth in claim 23, wherein the implantable pacemaker comprises a dual-chamber pacemaker that includes means for sensing P-waves and R-waves, means for generating A-pulses and V-pulses, and means for sensing a premature ventricular event (PVE); and further wherein the specific types of heart rate events that may be identified in each heart rate bin of the multi-event heart rate histogram comprise: (1) a P-wave followed by a V-pulse (referred to as a "PV" event); (2) a P-wave followed by an R-wave (referred to as a "PR" event); (3) an A-pulse followed by a V-pulse (referred to as an "AV" event); (4) an A-pulse followed by an R-wave (referred to as an "AR" event); and (5) a PVE; and further wherein all PV and PR events are considered to be sensed events, all AV and AR events are considered to be paced events, and all PVE events are considered to be premature events.

25. The external programmer, as set forth in claim 23, wherein the implantable pacemaker comprises a dual-chamber pacemaker that includes means for sensing P-waves and R-waves, means for generating V-pulses, and means for sensing a premature ventricular event (PVE); and further wherein the specific types of heart rate events that may be identified in each heart rate bin of the multi-event bin heart rate histogram comprise: (1) a P-wave followed by a V-pulse (referred to as a "PV" event); (2) a P-wave followed by an R-wave (referred to as a "PR" event); (3) a V-pulse (referred to as a "V" event); and (4) a PVE; and further wherein all PV and PR events are considered to be sensed events, all V events are considered to be paced events, and all PVE events are considered to be premature events.

26. The external programmer, as set forth in claim 11, wherein the display means includes a printer which prints a copy of the multi-event bin heart rate histogram on paper which can be removed from the external programmer.

27. A method of generating a multi-event bin heart rate histogram that depicts heart rate event data that has been sensed and recorded within an implantable pacemaker, the method comprising:
(a) retrieving the heart rate event data from the implantable pacemaker,
(b) sorting the heart rate event data as a function of type of event and rate of event;
(c) displaying the sorted heart rate event data in a multi-event heart rate histogram that comprises a graphical chart of the heart rate event data, wherein the graphical chart is made by:
(1) providing a multiplicity of heart rate bins arranged in order of increasing heart rate along a first axis of the graphical chart,
(2) creating a graphical representation of the number of heart rate events that occur within each heart rate bin, and
(3) providing an indication of at least three types of heart rate events that occur within each heart rate bin.

28. The method as set forth in claim 27, wherein the step of creating the graphical representation of the number of heart rate events that occur within each heart rate bin comprises:
making a display bar for each heart rate bin that extends out from the first axis by a length that indicates of the total number of heart rate events that have occurred within the respective heart rate bin.

29. The method as set forth in claim 28, wherein the step of providing an indication of the at least three types of heart rate events that occurs within each heart rate bin comprises dividing the event bar into a plurality of segments, with each segment being uniquely identifiable, and with each segment corresponding to, and having a length that represents the number of occurrences of, a specific type of heart rate event within the corresponding heart rate bin.

30. The method as set forth in claim 29, wherein the step of providing an indication of the at least three types of heart rate events that occurs within each heart rate bin comprises indicating paced events and sensed events.

31. The method as set forth in claim 30, wherein the step of providing an indication of the at least three types of heart rate events that occurs within each heart rate bin further comprises indicating premature events.

32. The method as set forth in claim 27, wherein the step of creating the graphical representation of the number of heart rate events that occur within each heart rate bin comprises:
making a display bar for each heart rate zone that extends out from the first axis a prescribed length, and
designating the prescribed length of the display bar to be representative of 100% of the number of heart rate events that have occurred within the respective heart rate bin, and
dividing the heart rate bin into a plurality of segments, with each segment having a length relative to the prescribed length of the display bar that is indicative of the number of occurrences of a specific type of heart rate event within the corresponding heart rate bin as compared with all of the occurrences of all of the heart rate events in that corresponding heart rate bin;
whereby the heart rate histogram provides a graphical indication of the heart rate event distribution by rate bin.

33. The method as set forth in claim 32, wherein the step of dividing the heart rate bin into a plurality of segments comprises dividing the heart rate bin into respective segments indicative of paced events and sensed events.

34. The method as set forth in claim 33, wherein the step of dividing the heart rate bin into a plurality of segments comprises dividing the heart rate bin into respective segments indicative of paced events, sensed events, and premature events.

35. An external programmer for use with an implantable pacemaker, the implantable pacemaker having means for sensing and recording heart rate event data, telemetry means for transferring the heart rate event data to the programmer, the external programmer comprising:
telemetry means for receiving the heart rate event data from the implantable pacemaker; and
means for displaying the heart rate event data in a multi-event heart rate histogram as a function of heart rate zone, the multi-event heart rate histogram comprising a 100% stacked histogram, the histogram including:
a plurality of heart rate bins arranged as a function of heart rate zone along a first axis;
an indication of at least two types of heart rate events in each heart rate bin; and
a display bar, extending from the first axis, that has a length that is representative of 100% of the number of heart rate events that have occurred within a respective heart rate zone, wherein the display bar of each heart rate zone is segmented into at least two portions corresponding to the at least two types of heart rate events;
whereby the heart rate histogram provides a graphical indication of the heart rate event distribution by rate zone.

36. The external programmer, as set forth in claim 35, the display bar comprises at least one portion corresponding to the percentage of sensed events that have occurred within the corresponding heart rate zone.

37. The external programmer, as set forth in claim 35, the display bar comprises at least one portion corresponding to the percentage of paced events that have occurred within the corresponding heart rate zone.

38. The external programmer, as set forth in claim 35, the display bar comprises at least one portion corresponding to the percentage of premature events that have occurred within the corresponding heart rate zone.

39. The external programmer, as set forth in claim 35, the display bar comprises at least three portions corresponding to the at least three types of heart rate events.

40. The external programmer, as set forth in claim 35, the display bar comprises:

a first portion corresponding to the percentage of sensed events that have occurred within the corresponding heart rate zone;

a second portion corresponding to the percentage of paced events that have occurred within the corresponding heart rate zone; and a third portion corresponding to the percentage of premature events that have occurred within the corresponding heart rate zone.

* * * * *